United States Patent
Hillbratt et al.

(10) Patent No.: US 9,900,709 B2
(45) Date of Patent: Feb. 20, 2018

(54) DETERMINING IMPEDANCE-RELATED PHENOMENA IN VIBRATING ACTUATOR AND IDENTIFYING DEVICE SYSTEM CHARACTERISTICS BASED THEREON

(71) Applicant: Cochlear Limited, Macquarie University, NSW (AU)

(72) Inventors: Martin E. Hillbratt, Lindome (SE); Kristian Asnes, Molndal (SE); Marcus Andersson, Gothenburg (SE); Johan Gustafsson, Gothenburg (SE); Mats Hojlund, Molnlycke (SE)

(73) Assignee: Cochlear Limited, Macquarie University, NSW (AU)

(*) Notice: Subject to any disclaimer, the term of this patent is extended or adjusted under 35 U.S.C. 154(b) by 563 days.

(21) Appl. No.: 14/212,116

(22) Filed: Mar. 14, 2014

(65) Prior Publication Data
US 2014/0286513 A1    Sep. 25, 2014

Related U.S. Application Data

(60) Provisional application No. 61/788,638, filed on Mar. 15, 2013.

(51) Int. Cl.
*H04R 25/00*    (2006.01)

(52) U.S. Cl.
CPC ......... *H04R 25/30* (2013.01); *H04R 2225/61* (2013.01); *H04R 2460/13* (2013.01)

(58) Field of Classification Search
CPC .... H04R 25/606; H04R 25/30; H04R 25/305; H04R 2225/67; A61N 1/36032
USPC ...... 381/326, 151, 380, 60, 58; 600/25, 559, 600/547; 607/115, 137, 116, 55–57
See application file for complete search history.

(56) References Cited

U.S. PATENT DOCUMENTS

| | | | |
|---|---|---|---|
| 8,325,964 B2 | 12/2012 | Weisman | |
| 8,965,012 B1* | 2/2015 | Dong | H04R 1/028 381/151 |
| 2003/0161492 A1 | 8/2003 | Miller et al. | |
| 2006/0247488 A1* | 11/2006 | Waldmann | H04R 25/30 600/25 |
| 2012/0286765 A1 | 11/2012 | Van den Heuvel et al. | |
| 2012/0300953 A1* | 11/2012 | Mauch | A61N 1/36032 381/60 |
| 2012/0316454 A1* | 12/2012 | Carter | A61B 5/053 600/547 |
| 2013/0018284 A1 | 1/2013 | Kahn et al. | |
| 2014/0072148 A1 | 3/2014 | Smith et al. | |
| 2014/0169597 A1* | 6/2014 | Gartner | H04R 25/305 381/314 |
| 2014/0270230 A1 | 9/2014 | Oishi et al. | |
| 2014/0275729 A1 | 9/2014 | Hillbratt et al. | |
| 2015/0256949 A1 | 9/2015 | Vanpoucke et al. | |
| 2016/0080878 A1 | 3/2016 | Hillbratt et al. | |
| 2016/0234613 A1 | 8/2016 | Westerkull | |

* cited by examiner

*Primary Examiner* — MD S Elahee
*Assistant Examiner* — Sabrina Diaz
(74) *Attorney, Agent, or Firm* — Hauptman Ham, LLP; Martin J. Cosenza

(57) ABSTRACT

A method, including determining a change in an actuator impedance based on a change in an electrical property of a system of which the actuator is apart, and determining one or more system characteristics based on the change in the actuator impedance.

43 Claims, 9 Drawing Sheets

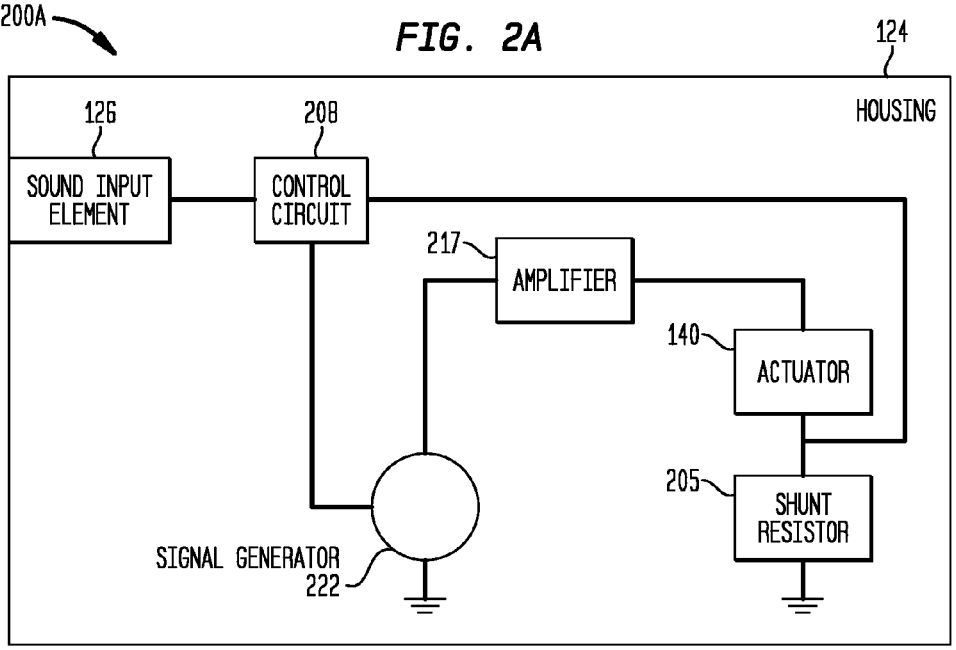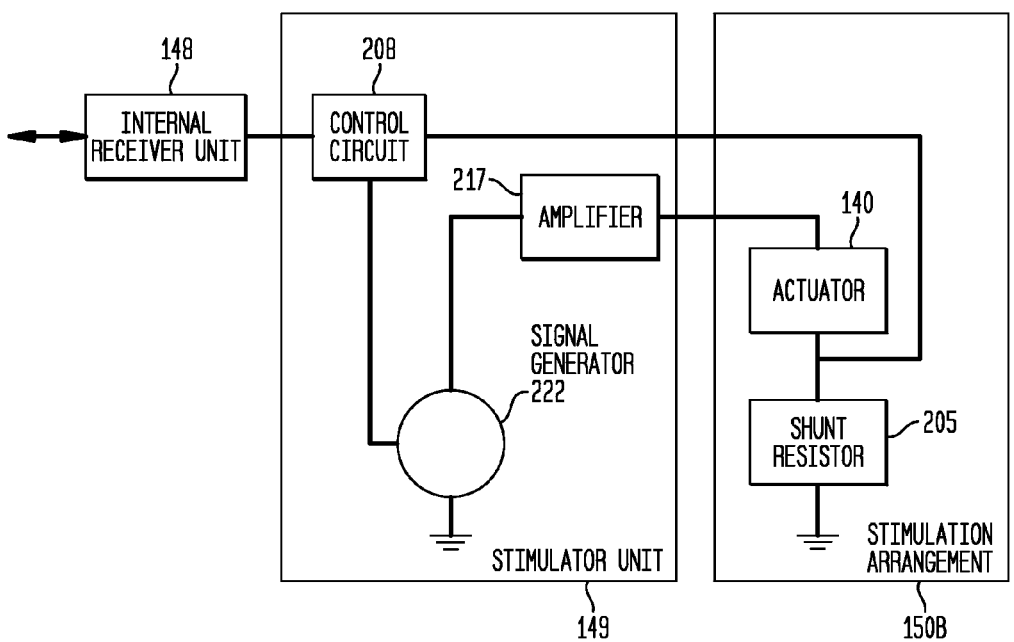

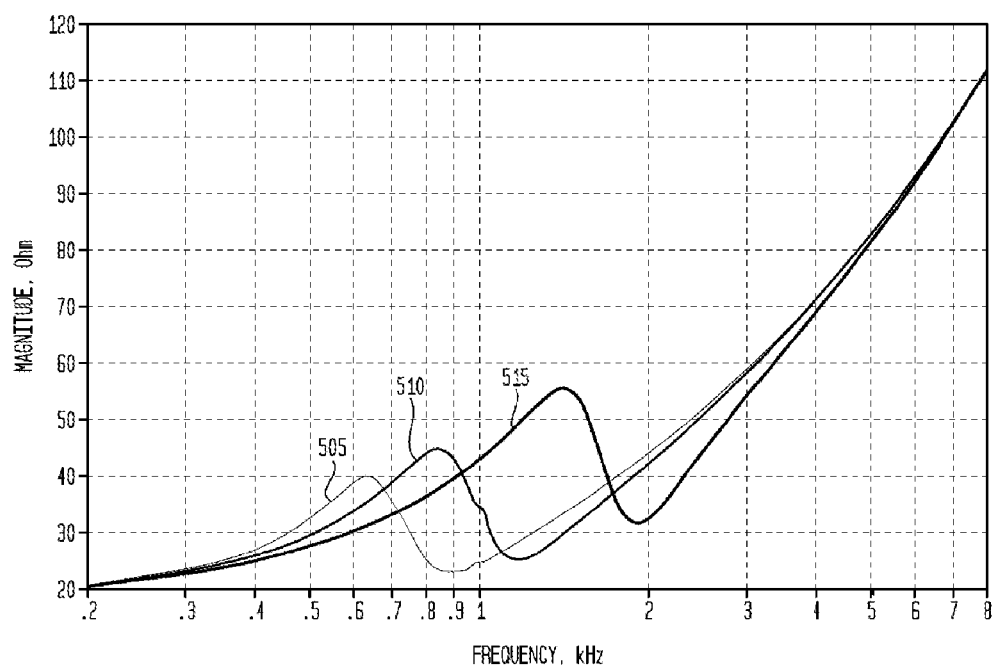

COIL IMPEDANCE PHASE FRF

DETERMINING IMPEDANCE-RELATED PHENOMENA IN VIBRATING ACTUATOR AND IDENTIFYING DEVICE SYSTEM CHARACTERISTICS BASED THEREON

CROSS-REFERENCE TO RELATED APPLICATIONS

This application claims priority to U.S. Patent Application Publication Ser. No. 61/788,638, entitled Measurement of Impedance in Vibrating Actuator and Identifying Actuator Characteristics, filed in the USPTO on Mar. 15, 2013, naming Martin Hillbratt as an inventor, the entire contents of that application being incorporated herein by reference in its entirety.

BACKGROUND

Field of the Technology

The present technology relates generally to hearing prostheses, and more particularly, to identifying system characteristics such as vibrating actuator characteristics, implant characteristics, coupling characteristics or other system characteristics in a hearing prosthesis.

Related Art

Hearing loss, which may be due to many different causes, is generally of two types, conductive and sensorineural. Sensorineural hearing loss occurs when there is damage to the inner ear, or to the nerve pathways connecting the inner ear to the brain. Conductive hearing loss occurs when the normal mechanical pathways that provide sound to the cochlea are impeded, for example, by damage to the ossicular chain or ear canal. However, individuals suffering from conductive hearing loss may retain some form of residual hearing because the hair cells in the cochlea may remain undamaged. As a result, individuals suffering from conductive hearing loss typically receive a hearing prosthesis that generates mechanical motion of the cochlea fluid. Still other individuals suffer from mixed hearing losses, that is, conductive hearing loss in conjunction with sensorineural hearing. Such individuals may have damage to the outer or middle ear, as well as to the inner ear (cochlea). Individuals suffering from conductive hearing loss typically receive an acoustic hearing aid. Unfortunately, not all individuals suffer from conductive hearing loss are able to derive suitable benefit from hearing aids.

Another type of hearing prosthesis delivers mechanical stimulation to a recipient. Such mechanical stimulating hearing prostheses include middle ear implants that deliver mechanical vibrations to the ossicles of the middle ear or directly to the cochlea, semicircular canals, vestibule or other part of the inner ear. Another type of mechanical stimulating hearing prosthesis, commonly referred to as a bone conduction devices, converts a received sound into mechanical vibrations that are delivered to the cranium, mandible or other part of the skull. The vibrations are transferred through the bones of the skull to the cochlea resulting in a hearing percept.

SUMMARY

According to an exemplary embodiment, there is a method, comprising determining a change in an actuator impedance based on a change in an electrical property of a system of which the actuator is apart, and determining one or more system characteristics based on the change in the actuator impedance.

According to another exemplary embodiment, there is a method comprising applying a first stimuli to an actuator that is part of a system, determining a change in voltage across a shunt component in series with the actuator, determining one or more system characteristics based on the change in voltage.

According to another exemplary embodiment, there is a hearing prosthesis, the prosthesis comprising an actuator, a signal generator configured to provide a signal to the actuator to cause actuation of the actuator, and a control circuit configured to direct the signal generator to apply a first stimuli to the actuator, wherein the control circuit is configured to determine a change in an electrical property of a system of which the actuator is apart, and determine an impedance-related phenomenon of the actuator based on the determined change in the electrical property.

According to another exemplary embodiment, there is a method for determining a state of an actuator of a hearing prosthesis configured to deliver mechanical stimulation to a recipient, comprising, measuring a first voltage across a shunt component in series with the actuator, comparing the first voltage with a second voltage, and determining one or more characteristics of the hearing prosthesis.

BRIEF DESCRIPTION OF THE DRAWINGS

Embodiments of the present technology are described below with reference to the attached drawings, in which:

FIG. 2A illustrates a simplified block diagram of a housing of an exemplary bone conduction device in which embodiments of the present technology may be implemented;

FIG. 2B illustrates a simplified block diagram of a stimulator unit and stimulation arrangement of a middle ear implant in which embodiments of the present technology may be implemented;

FIG. 5A is frequency responses for the magnitude of the impedance of an actuator in which embodiments of the present technology may be implemented.

DETAILED DESCRIPTION

Aspects and embodiments of the present technology are directed to mechanical stimulating hearing prostheses, and more particularly, to determining characteristics, behavior or state of an actuator of the prosthesis based on changes in the mechanical impedance of the actuator.

The mechanical impedance of an actuator in a mechanical stimulating hearing prosthesis may be used to improve the accuracy of mechanical stimulation delivered to the recipient and may be used to detect a characteristic, behavior or state of the system (e.g. the type of system, if an implanted actuator, turned off or disconnected, the stability of the system, etc.). More specifically, a change in impedance of the actuator may indicate a change in such a characteristic, behavior or state (as referred to herein, the term "characteristic" may also refer to the "status," "state," or "behavior" of the actuator, or vice versa). For example, an increase in impedance of the actuator may indicate that an implanted actuator has become more unstable or, for a more drastic increase, that the implanted actuator has been detached from the recipient.

Exemplary embodiments are disclosed for measuring impedance and changes in impedance of an actuator in such a hearing prosthesis. A shunt component, such as a shunt resistor, may be connected in series to the actuator, and the voltage measured across the shunt resistor in response to a stimulus may be used to determine the impedance across the actuator. Exemplary embodiments of the present technology are described herein with respect to two exemplary mechanical stimulating hearing prostheses, namely an exemplary bone conduction device illustrated in FIG. 1A, and an exemplary middle ear hearing prosthesis illustrated in FIG. 1B.

Figure 1A:
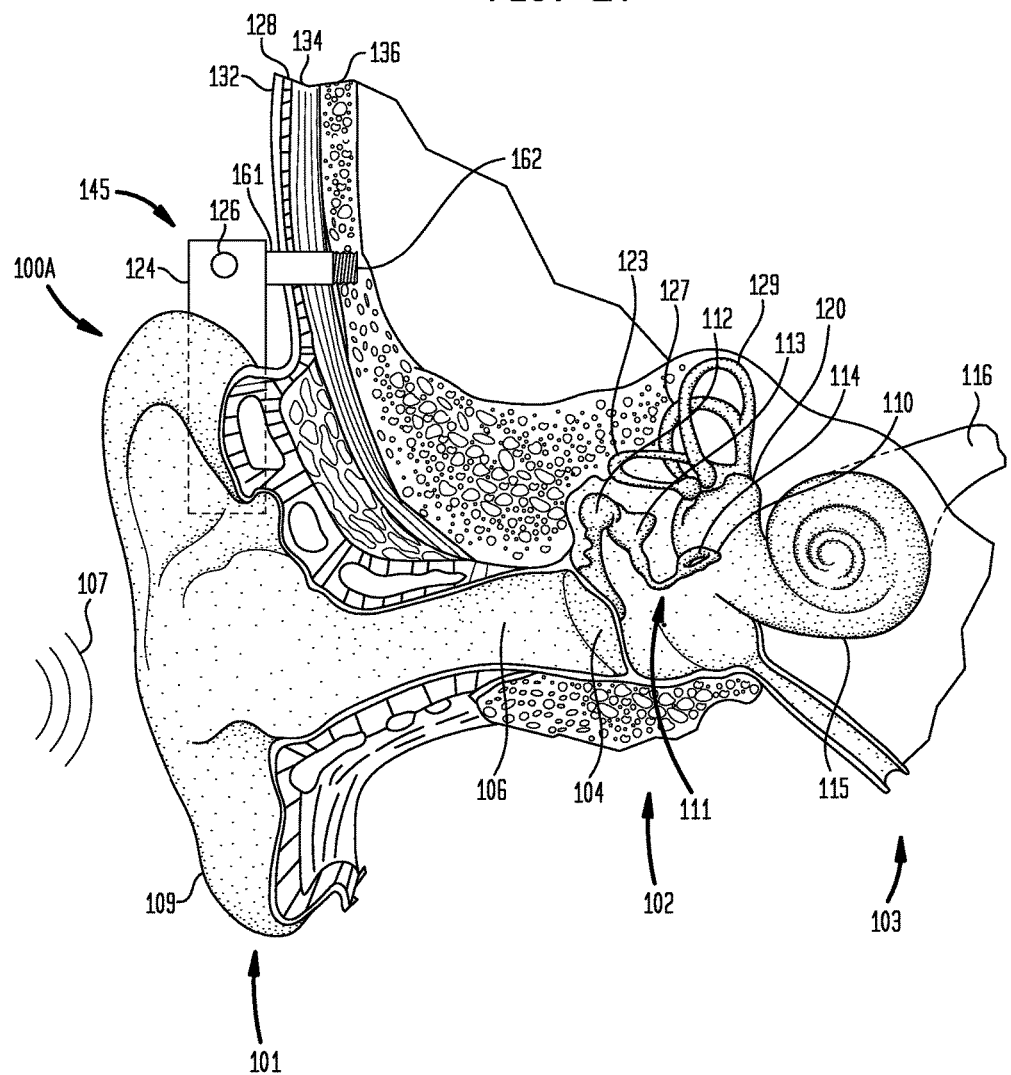
FIG. 1A is a perspective view of a percutaneous bone conduction hearing prosthesis in which embodiments of the present technology may be implemented.

FIG. 1A is a perspective view of a percutaneous bone conduction device 100A in which embodiments of the present technology may be advantageously implemented. As shown, the recipient has an outer ear 101, a middle ear 102 and an inner ear 103. Elements of outer ear 101, middle ear 102 and inner ear 103 are described below, followed by a description of bone conduction device 100A.

In a fully functional human hearing, outer ear 101 comprises an auricle 109 and an ear canal 106. A sound wave 107 is collected by auricle 109 and channeled into and through ear canal 106. Disposed across the distal end of ear canal 106 is a tympanic membrane 104 which vibrates in response to sound wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify sound wave 107, causing oval window 110 to articulate, or vibrate. Such vibration activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1A also illustrates the positioning of bone conduction device 100A relative to outer ear 101, middle ear 102 and inner ear 103 of a recipient of device 100A. As shown, bone conduction device 100A includes external component 145 which may be positioned behind outer ear 101 of the recipient and comprises a sound input device 126 to receive sound signals. Sound input device may comprise, for example, a microphone, telecoil, etc. Sound input device 126 may also be a component that receives an electronic signal indicative of sound, such as, for example, from an external audio device. For example, sound input device 126 may receive a sound signal in the form of an electrical signal from an MP3 player electronically connected to sound input device 126. Sound input device may be located, for example, on the device, in the device, or on a cable extending from the device.

Bone conduction device 100A may comprise a sound processor, a vibrating actuator and/or various other operational components which facilitate operation of the device. More particularly, bone conduction device 100A operates by converting the sound received by sound input device 126 into electrical signals. These electrical signals are utilized by the sound processor to generate control signals or driver signals (also referred to herein as "stimuli") that cause the actuator (located in housing 124) to vibrate. These control signals are provided to the vibrating actuator. As described below, the vibrating actuator converts the signals into mechanical vibrations used to output a force for delivery to the recipient's skull.

Bone conduction device 100A further includes a housing 124, a coupling 161 and an implanted anchor 162 configured to attach the device to the recipient. In the specific embodiments of FIG. 1A, coupling 161 is attached to implanted anchor 162, which is implanted in the recipient. In the illustrative arrangement of FIG. 1A, implanted anchor 162 is fixed to the recipient's skull bone 136. Coupling 161 extends from implanted anchor 162 and bone 136 through muscle 134, fat 128 and skin 132 so that housing 124, or a component within housing 124, may be attached thereto. Implanted anchor 162 facilitates efficient transmission of mechanical force to the recipient. It would be appreciated that embodiments of the present technology may be implemented with other types of couplings and anchor systems, as well as other types of bone conduction devices, such as, for example, an active or passive transcutaneous bone conduction device (including, for example, transmission of data to the recipient's skull using a magnetic field, a magnet attached to the outside of the recipient's head and an another magnet implanted in the recipient's skull).

Figure 1B:
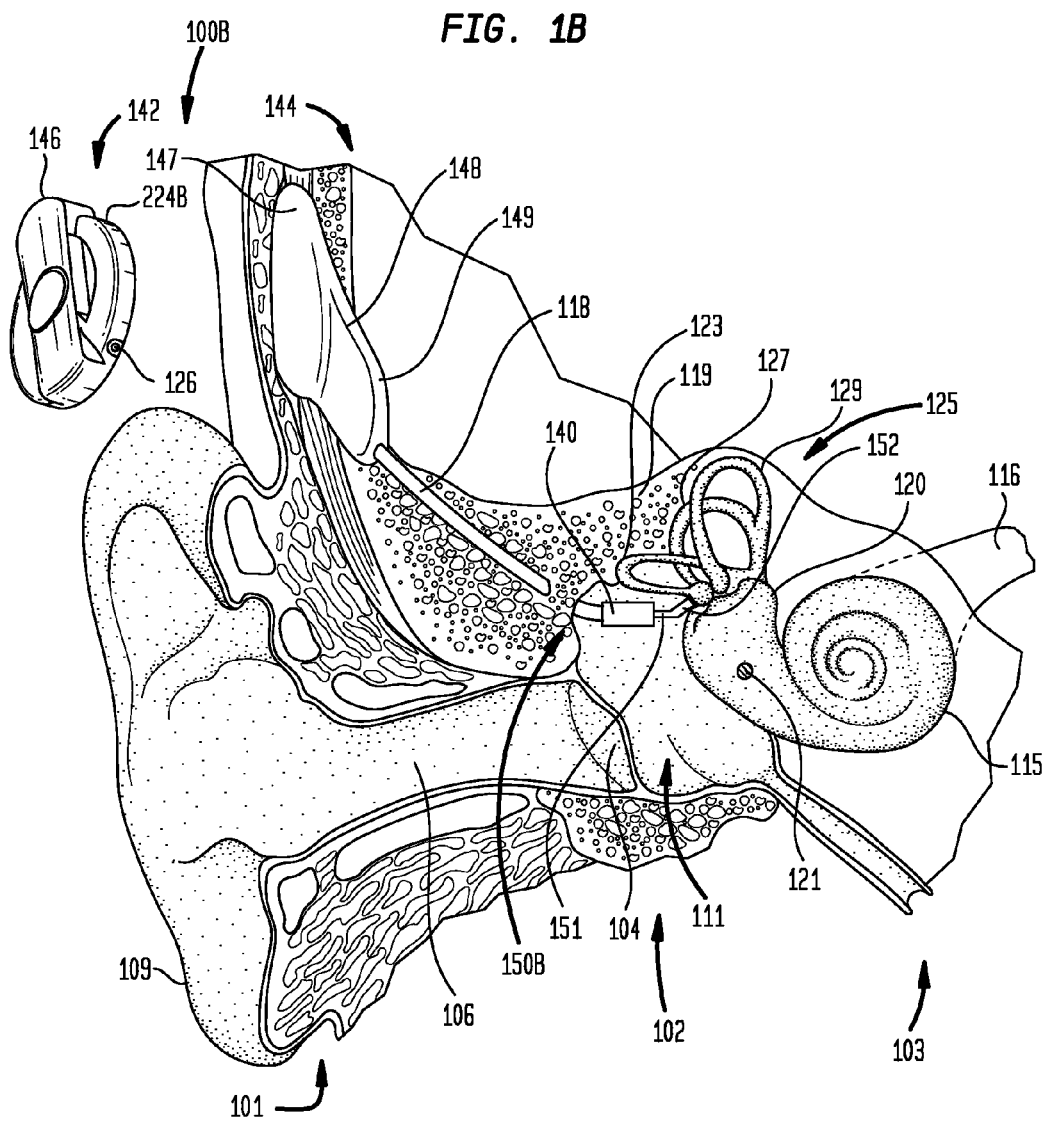
FIG. 1B is a perspective view of a middle ear hearing prosthesis in which embodiments of the present technology may be implemented.

Embodiments of the present technology may also be implemented to include a middle ear hearing prosthesis, as noted. A middle ear hearing prosthesis generates vibrations that are directly coupled to the middle ear of a recipient and thus bypasses the outer ear of the recipient. FIG. 1B is a perspective view of an exemplary middle ear hearing prosthesis 100B in accordance with embodiments of the present technology.

Middle ear hearing prosthesis 100B comprises an external component 142 that is directly or indirectly attached to the body of the recipient, and an internal component 144 that is temporarily or permanently implanted in the recipient. External component 142 typically comprises one or more sound input devices, such as microphones 224 for detecting sound, a sound processing unit 146, a power source (not shown), and an external transmitter unit (also not shown). The external transmitter unit is disposed on the exterior surface of sound processing unit 146 and comprises an external coil (not shown). Sound processing unit 146 processes the output of microphones 224 and generates encoded signals, sometimes referred to herein as encoded data signals, which are provided to the external transmitter unit. For ease of illustration, sound processing unit 146 is shown detached from the recipient.

Internal component 144 comprises an internal receiver unit 148, a stimulator unit 149, and a stimulation arrangement 150B. Internal receiver unit 148 and stimulator unit 149 are hermetically sealed within a biocompatible housing, sometimes collectively referred to herein as a stimulator/receiver unit.

Internal receiver unit 148 comprises an internal coil (not shown), and preferably, a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 is positioned in a recess of the temporal bone adjacent auricle 109 of the recipient in the illustrated embodiment.

In the illustrative prosthesis, stimulation arrangement 150B is implanted in middle ear 102. For ease of illustration, ossicles 111 have been omitted from FIG. 1B. However, it should be appreciated that stimulation arrangement 150B is implanted without disturbing ossicles 111 in the illustrated embodiment.

Stimulation arrangement 150B comprises an actuator 140, a stapes prosthesis 152 and a coupling element 151. In this embodiment, stimulation arrangement 150B is implanted and/or configured such that a portion of stapes prosthesis 152 abuts an opening in one of the semicircular canals 125. For example, in the illustrative prosthesis, stapes prosthesis 152 abuts an opening in horizontal semicircular canal 123. It would be appreciated that in other middle ear hearing prostheses, stimulation arrangement 150B may be implanted such that stapes prosthesis 152 abuts an opening in posterior semicircular canal 127 or superior semicircular canal 129. It would also be appreciated that stimulation arrangement 150B may be implanted such that stapes prosthesis 152 abuts round window 121 or other structure that will result in the delivery of mechanical energy to the hydro-mechanical system of the cochlea.

As noted above, a sound signal is received by one or more microphones 224, processed by sound processing unit 146, and transmitted as encoded data signals to internal receiver 148. Based on these received signals, stimulator unit 149 generates drive signals which cause actuation of actuator 140. This actuation is transferred to stapes prosthesis 152 such that a wave of fluid motion is generated in horizontal semicircular canal 123. Because, vestibule 120 provides fluid communication between the semicircular canals 125 and the median canal, the wave of fluid motion continues into median canal, thereby activating the hair cells of the organ of corti. Activation of the hair cells causes appropriate nerve impulses to be generated and transferred through the spiral ganglion cells (not shown) and auditory nerve 116 to the brain (also not shown) where they are perceived as sound.

As noted, the prostheses of FIGS. 1A and 1B are but two exemplary mechanical stimulating hearing prostheses. Embodiments of the present technology may be implemented in connection with other types of mechanical stimulating hearing prostheses now or later developed. However, for ease of description, the following description of embodiments of the present invention are described, where applicable, with reference to a percutaneous bone conduction device an example of which, bone conduction device 100A, is introduced above with reference to FIG. 1A.

As noted, the impedance of an actuator in a vibrating hearing prosthesis, such as those described in FIG. 1A, may be used to improve the accuracy of mechanical stimulation delivered to the recipient and may be used to detect a characteristic, behavior or state of the system (e.g. the type of system, if an implanted actuator, turned off or disconnected, the stability of the system, etc.). More specifically, a change in mechanical impedance of the actuator may represent a change in a state or characteristic of the actuator or the hearing prosthesis as a whole. Furthermore, a change in electrical impedance presented by the actuator indicates a corresponding change in mechanical impedance of the actuator. As is known to one of skill in the art, resonance refers to the tendency of a system to oscillate with larger amplitude at some frequencies than at others. Therefore, the frequency response of the electrical impedance of an actuator is used to observe such changes in mechanical impedance between different frequencies, different times and different actuators. Exemplary frequency responses are discussed with respect to FIGS. 5A and 5B.

Figure 5B:
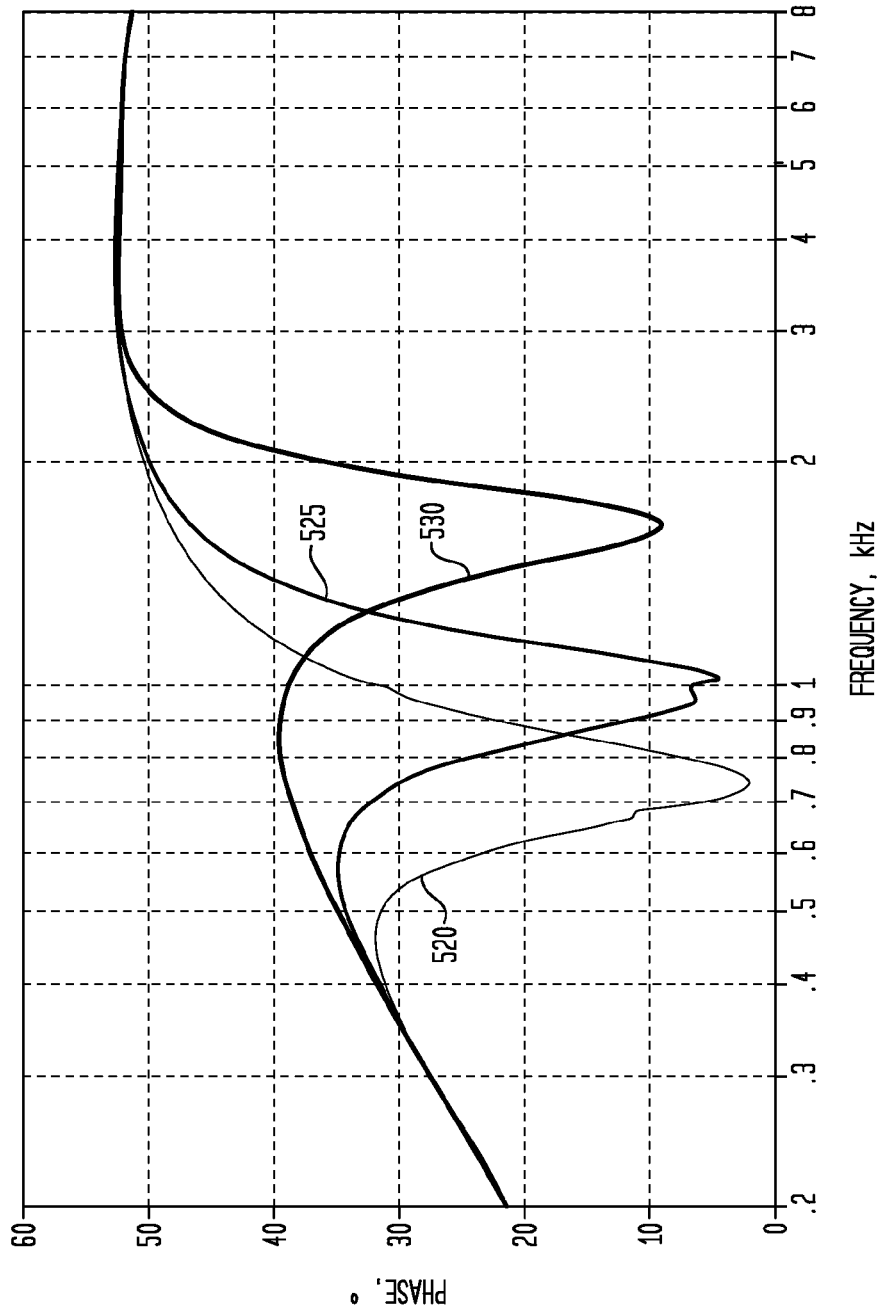
FIG. 5B is frequency responses for the phase of the impedance of an actuator in which embodiments of the present technology may be implemented.

FIG. 5A illustrates a frequency response for the magnitude of the electrical impedance (hereinafter "impedance magnitude") of, for example, the actuator in FIG. 1A. FIG. 5B illustrates the corresponding frequency response for the phase of the impedance of the actuators, and will be described further below. Frequency responses 505, 510 and 515 may be obtained in many different ways known in the art, such as applying a sine/frequency sweep to obtain response values for each of a variety of frequencies across a chosen frequency range (such as, for example, the operational frequency range of the actuator/bone conduction device). Each exemplary actuator is in a different state. Frequency response plot 505 represents the frequency response for the impedance magnitude of an actuator that is securely attached or fully osseointegrated to the recipient. It should be recognized that "fully" osseointegrated as used herein may include an actuator, or an implanted anchor such as implanted anchor 162 to which the actuator is connected, that is substantially, or almost, osseointegrated into the skull of a recipient such that the osseointegration is sufficient for the recipient to use the actuator as a component of a hearing prosthesis without causing damage to the actuator or to the recipient. For example, the actuator is not unstable or loose from the head of the recipient that it is attached to. Since a stable actuator connection is ideal for a bone conduction device that is coupled to a recipient using a rigid percutaneous abutment, this state of the actuator may be considered below to be an "ideal" actuator state for that type of connection, as will be described further. Frequency response plot 510 represents the frequency response for the impedance magnitude of an actuator that is unstable, or loosely attached to the recipient. For example, the actuator may be damaged, the implant may be loose, or the implant may have not fully osseointegrated with the bone of the recipient with which it is attached after surgery. In another embodiment, the actuator may be held by a softband that is configured to be worn around the recipient's head. In other embodiments, the actuator may be connected to the skull of the recipient using an adhesive, a testband, test rod, a transcutaneous device using transmission of data via magnets, or other types of bone conduction devices including actuators that are not implanted in the skull of the recipient. When a softband or other non-implanted system is used, the actuator may be pushed against the recipient's skull to transmit vibrations to the skull, but is not rigidly connected to the skull. Frequency response plot 515 represents the frequency response for the impedance magnitude of an actuator that is disconnected from the recipient. For example, the actuator may be held in the recipient's hand or may be lying on a table while the recipient is sleeping.

As can be seen in FIG. 5A, frequency responses 505, 510 and 515 of the magnitude of the impedances of the actuator across the chosen frequency range vary. For example, between the frequencies of approximately 0.4 kHz (400 Hz)

and 4 kHz (4000 Hz), frequency response plots 505, 510 and 515 show varying magnitudes. More specifically, at those frequencies, the actuator has different magnitudes of impedance across it. The comparison of plots 505, 510 and 515 shows that when the impedance across the actuator varies, the actuator may have different stabilities or may be connected to the recipient in different ways (again, referred to herein as actuator characteristics or states), as will be described further.

Embodiments include various techniques that can use impedance data provided by an actuator, such as the data in the frequency responses shown in FIG. 5A for the magnitude of the impedance of the actuator, to make determinations about the state of the actuator. For example, first, the magnitude of the impedance of an actuator may be compared to a threshold, such as the magnitude of the impedance of a predetermined "ideal" (i.e. ideally stable) actuator. For example, if the actuator is integrated into a bone conduction device, then the threshold "ideal" or expected frequency response may be, for example, (1) the frequency response of the same actuator taken at a time when the device was known to be stable and fully osseointegrated into the skull of the recipient, (2) the frequency response of a different device that is stable and fully osseointegrated into the same recipient at a previous time, or (3) the frequency response of the actuator taken from a simulation. This process may be completed by, for example, an audiologist when examining a recipient after the recipient has undergone surgery to implant a bone conduction device.

For example, as noted, frequency response plot 505 could be used as a threshold, or in other words the frequency response of an actuator taken at a time when the device was known to be stable and fully osseointegrated into the skull of the recipient. Then, when running a test on a recipient, an audiologist may compare corresponding data taken from the recipient's actuator to the threshold data. The audiologist may receive and analyze raw data, or may receive a result/conclusion after the raw data has already been analyzed by the DSP within the device. Such a result may include a conclusion that the actuator is unstable, or an even more specific conclusion such as, for example, that the actuator is unstable and will require three more days until stability is reached at the (then) current rate of osseointegration. If frequency response plot 510 was taken as the frequency response representing an actuator being used in a hearing prosthesis of a recipient, then the system or an audiologist may compare frequency response plot 510 with threshold frequency response plot 505 to observe any differences in impedance magnitude. More specifically, the audiologist may select one or more frequencies for which to compare the impedance magnitude (in this example, by comparing plot 510 with the threshold impedance magnitude of plot 505). For example, if the audiologist selected a frequency of 1 kHz, then the comparison would show an impedance magnitude of approximately 35 Ohms as compared to a threshold impedance magnitude of approximately 25 Ohms, as shown by plots 505 and 510 in FIG. 5A. The difference of 10 Ohms between the measured value and threshold value would indicate to the audiologist that the recipient's actuator is, for example, unstable. In other words, the increase in impedance magnitude would indicate a move from more a stable to a less stable implant.

In an exemplary embodiment, the magnitude of the impedance of the actuator can be determined through the use of two different measurements obtained at or during the same temporal period (e.g., simultaneously). By way of example only and not by way of limitation, a voltage and a current across an actuator can be determined. That said, alternatively and/or in addition to this, voltage and/or current determinations can be made at other locations, such as, for example, voltage output from an amplifier. Any device, system and/or method that can enable the magnitude and/or phase of the impedance of the actuator to be determined can be utilized in at least some embodiments.

Referring again to FIG. 5A, if plot 515 represents the frequency response of the magnitude impedance of the recipient's actuator, then an audiologist may compare frequency response plot 515 with threshold frequency response plot 505 to observe any differences in impedance magnitude. If the audiologist selected the same frequency of 1 kHz for comparison, then the comparison would show an impedance magnitude of approximately 44 Ohms as compared to a threshold impedance magnitude of approximately 25 Ohms. The difference of 19 Ohms between the measured value and threshold value would indicate to the audiologist that the recipient's actuator is even more unstable. For example, such a difference may indicate to the audiologist that the actuator is not connected to the recipient's skull at all, and instead is either in the recipient's hand or lying on a table while the recipient is sleeping.

As noted, the DSP or audiologist may read the magnitude impedance of more than one frequency. If the DSP or audiologist were to only read impedance data for one sample frequency, the comparison of this impedance data to the threshold data at that frequency may yield a false negative. For example, if the audiologist chose 700 Hz, then both representative plot 510 and 505 would yield a magnitude of approximately 38 Ohms. The audiologist may then assume that the implant is fully stable although, as shown by magnitude impedance data for most other frequencies between 400 Hz and 4 kHz, the actuator is in fact unstable or loose.

As noted, an actuator may be held by a passive transcutaneous, softband or testband bone conduction device or may be connected to the head in other ways, such as via an adhesive. For such a device, the "ideal" or threshold magnitude impedance may be represented a less stable frequency response since such a system provides for the actuator to be, as noted, pushed up against the recipient's skull to transmit vibrations to the skull, but not rigidly connected to the skull. Therefore, the threshold magnitude impedance frequency response may be plot 510 instead of plot 505.

Referring back to FIG. 5A, if the audiologist selected a frequency of 800 Hz, the comparison would show an impedance magnitude of approximately 25 Ohms as compared to a threshold impedance magnitude of approximately 35 Ohms. While such a comparison would show a decrease in magnitude impedance, this difference also represents a change in impedance and may also indicate a shift in the stability of the actuator. A drastic decrease in magnitude impedance may indicate that the actuator has been re-connected to the skull of the recipient after being previously decoupled after an accident or removal by the recipient for sleeping or another purpose.

Some exemplary embodiments will be detailed herein that enable the determination of a change in the impedance of the actuator. It is noted that any device, system and/or method that can enable a determination that a change of an impedance of the actuator has taken place can be utilized in at least some embodiments.

It is further noted that a change in the overall system can result in a change in the impedance of the actuator. As is explained in more detail elsewhere, the actuator itself may not change, but the system in which it is used may change (e.g., mechanical aspects of a coupling that places the actuator in vibrational communication with the recipient can change over time, and this will result in a change in the impedance of the actuator because it is mechanically linked to the coupling).

Furthermore, the magnitude of the impedance may instead be observed for differences in magnitude between multiple frequencies. More specifically, the audiologist may read the magnitude of the impedance at two different frequencies, calculate the difference in magnitude between the two frequencies, and then compare that difference to a threshold. For example, the audiologist could calculate the difference in magnitude between 0.7 kHz (700 Hz) and 0.9 Hz (900 Hz). If frequency response plot 510 represents the frequency response of the recipient's actuator, then the difference in impedance magnitude between 700 and 900 Hz would be calculated by the audiologist as an increase of approximately 4 Ohms (from 39 Ohms to 43 Ohms). If plot 505 represents the frequency response threshold, the threshold difference between the two frequencies would be approximately 10 Ohms (from 37 Ohms to 27 Ohms). This change in the difference between magnitudes of impedance at different frequencies would indicate to the audiologist that the recipient's implant has changed in stability, such as, for example, indicating a shift from more a stable to a less stable actuator.

A second technique that uses impedance data provided by an actuator to make a determination of the state of the actuator is to observe the magnitude of the impedance of an actuator for changes over time. For example, an audiologist may observe magnitude impedance data from the recipient's actuator at a certain selected frequency, and then compare that data to similar data from the actuator at the same frequency at a later time. If a change in the magnitude of impedance across the actuator is different at the later time, then this change in impedance may indicate a change in state or characteristic of the actuator, such as that an implant has become more unstable or, for a more drastic increase, that the device has been detached from the recipient altogether. For example, if the frequency response of the magnitude impedance of the actuator at a certain frequency at a first time was represented by plot 505, and the audiologist chose to sample the magnitude impedance at 0.6 kHz (600 Hz), then the audiologist would read a magnitude of about 39 Ohms. If the actuator became loose, was detached from the head or was otherwise adjusted by accident or on purpose, then that magnitude may change accordingly. Therefore, if the audiologist reads the magnitude impedance at the same 0.6 kHz (600 Hz) frequency at a later time, the magnitude may be higher or lower than 39 Ohms, indicating such a change in status of the actuator. For example, if the frequency response of the magnitude impedance of the actuator at the later time was represented by plot 510, then the audiologist would read a magnitude of about 34 Ohms. The 5 Ohm drop between two different times (which may be less than a second, seconds, minutes, hours, days or months apart) represents, as noted, a change in status such as a change in stability of the device.

Third, magnitude of the impedance of an actuator may be observed using resonance peaks of the frequency response of the magnitude impedance of the actuator. A resonance peak of a frequency response refers to the frequencies or frequencies at which a peak in the amplitude of the frequency response of the system occurs. Therefore, observing and comparing resonance peaks of the frequency response of the magnitude impedance to either the expected resonance peak of the frequency response of the magnitude impedance for an "ideal" actuator connection with the recipient, such as the threshold frequency response described, or to the resonance peak of the frequency response of the magnitude impedance at a previous point in time, may indicate a change in state of the actuator.

FIG. 5B illustrates three frequency responses for the phase of the impedance (hereinafter "impedance phase") of, for example, the actuator in FIG. 1A. Frequency response plot 520 represents the frequency response for the impedance phase of an actuator that is securely attached to the recipient (and, for example, not unstable or loose). Frequency response plot 525 represents the frequency response for the impedance phase of an actuator that is unstable, or loosely attached to the recipient. Frequency response plot 530 represents the frequency response for the impedance phase of an actuator that is disconnected from the recipient. Similar conclusions may be drawn from the frequency response for the impedance phase of an actuator as from the frequency response for the impedance magnitude of that actuator. For example, the phase of the impedance of an actuator may be compared to a threshold, such as the phase of the impedance of a predetermined expected, ideal or baseline actuator. The phase of the impedance of an actuator may also be observed for changes over time. Furthermore, the phase of the impedance of an actuator may be observed using resonance peaks of the frequency response of the phase impedance of the actuator.

As can be seen in FIG. 5B, the actuator has varying frequency responses of the phase of its impedance in different states. For example, between the frequencies of approximately 0.4 kHz (400 Hz) and 3 kHz (3000 Hz), frequency response plots 520, 525 and 530 show varying phases. More specifically, at those frequencies, the actuator has different phases of impedance across it. This comparison represents that the actuator may have different stabilities or may be connected to the recipient in different ways, as described above with respect to magnitude. One of ordinary skill in the art would appreciate that similar techniques as those described above with respect to observing changes in the magnitude impedance of an actuator may be applied similarly to changes in the phase impedance of an actuator.

Embodiments of the present technology have been discussed with reference to measuring and storing data related to frequency responses of the impedance of an actuator for the purpose of an audiologist using that data to make assumptions about the status or characteristics of the hearing prosthesis. However, the data may also be used internally by the device itself to, as noted, improve the accuracy of mechanical stimulation delivered to the recipient. More specifically, the frequency response of the impedance across an actuator in a bone conduction device is used by the stimulator unit, such as stimulator unit 149 in FIG. 1A, in generating the drive signals provided to the actuator in processing received sound and causing a hearing percept by the recipient. For example, in certain embodiments, as noted, the actuator may have sharp resonance peaks, which indicate a spike in impedance across the actuator. For another example, changes in impedance across an actuator may otherwise indicate that the actuator is unstable, that the actuator is being used in a softband, or other functional states. Measuring the frequency response (and, for example, determining resonance peaks of the frequency response) by measuring changes in impedance of the actuator, allows the stimulator unit to compensate for (e.g., using software) the instability of the system, resonance peaks or other problems with the actuator. For example, the control circuit (e.g. DSP) may compensate for a lower transmission of sound to the cochlea by the softband, re-calibrate the frequency response output levels, among other remedies. Depending on the actuator type this compensation may be useful for different reasons. For example, sharp changes in resonance or actuator impedance can cause feedback to occur at those frequencies. Further, such changes can result in the power consumption becoming too high, distortion of the stimulation since the actuator may start to behave non-linearly, or even over-stimulation that may result in hearing damage if not properly controlled.

As would be appreciated by one of ordinary skill in the art, the data shown in FIGS. 5A and 5B, including magnitudes, phases and frequencies, are provided for illustration purposes only. The actual data may vary depending on the individual and application of the present technology. As such, these illustrative examples should not be construed as limiting the present invention.

Exemplary devices for measuring changes in impedance of an actuator in such a vibrating hearing prosthesis are described below with respect to FIGS. 2A and 2B. For ease of explanation, only those components of the bone conduction device that will be discussed below are illustrated in FIGS. 2A and 2B, and in actual implementation additional components may be included, such as actuator drive components, etc.

FIG. 2A is a simplified block diagram of a housing of an exemplary bone conduction device 200A, such as the bone conduction device of FIG. 1A. As illustrated, housing 124 includes a sound input device 126, a control circuit 208, a signal generator 222, an amplifier 217, an actuator 140 and a shunt resistor 205. Control circuit 208 is a circuit configured for exercising control over the bone conduction device. For example, control circuit 208 is configured for receiving, from the sound input device 126, sound waves from the recipient's environment. Furthermore, control circuit 208 is configured to process the audio signals to generate control signals for controlling signal generator 222 in generating drive signals causing actuation of actuator 140. Control circuit 208 may include a digital signal processor (DSP) and/or other components to control the other components within housing 124. Alternatively the control circuit 208 may comprise a controller such as a microprocessor or a software based controller. The control circuit 208 may comprise either digital circuitry or analog circuitry. It should be understood the term control circuit can include any control device or system.

Signal generator 222, as noted above, generates the drive signals for causing actuation of actuator 140. After signal generator 222 sends a drive signal towards actuator 140, it is amplified by amplifier 217. Amplifier 217 is controlled by control circuit 208 and, in conjunction with signal generator 222, determines the amplitude and other characteristics of the drive signal sent to actuator 140. Actuator 140 is any type of suitable transducer configured to receive electrical drive signals and generate mechanical motion (e.g. vibrations) in response to the received electrical signals.

Shunt resistor 205 is electrically connected in series to actuator 140, and may be used for the purpose of measuring the impedance across actuator 140. A shunt resistor, also known as an ammeter shunt, is a low resistance precision resistor used to measure AC or DC electric currents. However, a shunt resistor may include various other types of resistive elements, instead of or in addition to a typical, stand-alone shunt resistor, used to represent such a low resistance path, such as electrostatic discharge (ESD) components. Such ESD components may be otherwise present in housing 124 to relieve the system of static that could damage wires or other components within any integrated circuitry in housing 124. Therefore, no extra components may be necessary to provide a shunt resistor for measuring impedance. Shunt resistors generally allow electric currents to pass through it by creating a low resistance path that attracts current towards that path and has a measurable change in electrical impedance either in the time domain or in the frequency domain. Collectively, components such as shunt resistors or other resistive elements that act similar to shunt resistors for the purpose of providing a low resistance path, as described above, may be called "shunt components." Examples of such shunt components may include typical, stand-alone shunt resistors, electrostatic discharge (ESD) components, capacitors, diodes, among others.

FIG. 2B is a simplified block diagram of a stimulator unit and stimulation arrangement of an exemplary middle ear implant. The components of system 200B are similar to bone conduction device 200A, except that the components are divided in between stimulator unit 149 and stimulation arrangement 150B. For example, as shown in FIG. 2B, control circuit 208, signal generator 222 and amplifier 217 may be included within stimulator unit 149, while actuator 140 and shunt resistor 205 may be included within stimulation arrangement 150B. Alternatively, shunt resistor 205 may be included within control circuit 208 or otherwise within stimulator unit 149. It would also be appreciated by a person of ordinary skill in the art that other combinations of components, including extra components not shown in FIG. 2A or 2B, are also contemplated within the scope of the current technology.

To determine a change in impedance across actuator 140, shunt resistor 205 may be used. For example, since shunt resistor 205 has a known resistance at manufacture, the voltage across shunt resistor 205 is proportional to the current flowing through shunt resistor 205. Furthermore, since shunt resistor 205 is connected to actuator 205 in series, the current flowing through shunt resistor 205 is substantially the same as the current flowing through actuator 140. Therefore, measuring the voltage across shunt resistor 205 can be used to evaluate the impedance across actuator 140 (including detecting a change of impedance or the impedance) and determining a change in voltage across shunt resistor 205 indicates a change in mechanical impedance across actuator 140. Therefore, determining a change in voltage across shunt resistor 205 corresponds to and/or is representative of a change in electrical impedance across actuator 140 and, in turn, a change in mechanical impedance across actuator 140 for a given stimulus. Therefore, a change in the voltage across shunt resistor 205 is indicative of a change of impedance across actuator 140.

Figure 3A:
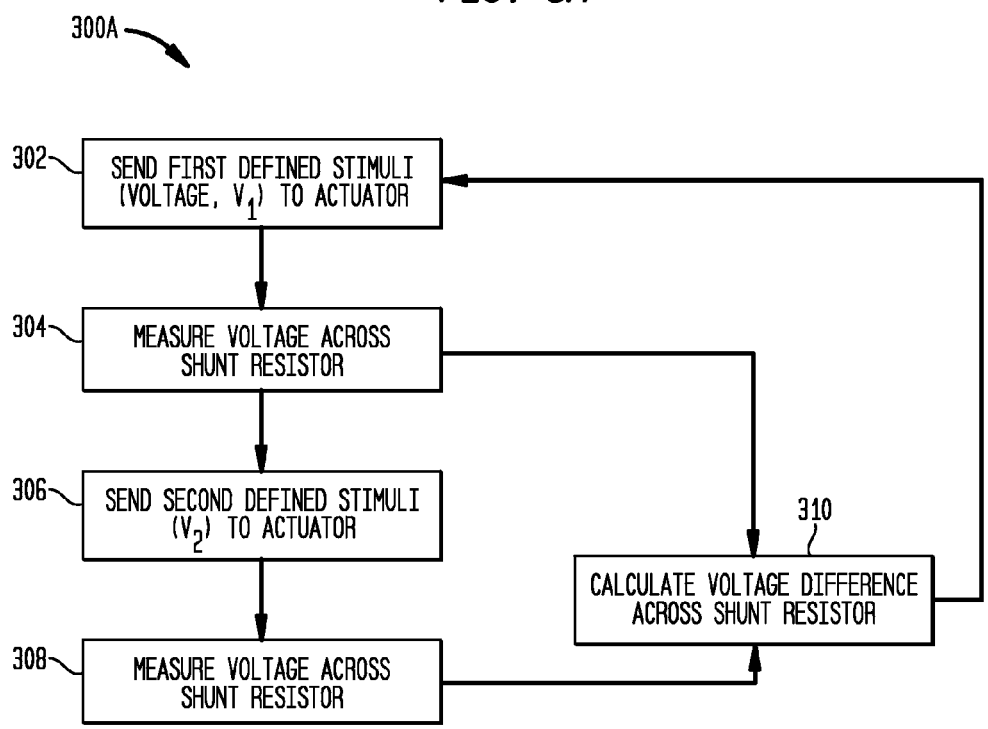
FIG. 3A illustrates a flow chart of an exemplary method for determining a change in impedance across an actuator using a shunt component.

FIG. 3A is a flow chart 300A of an exemplary method for determining a change in impedance across actuator 140 using shunt resistor 205. First, as shown in block 302, a defined stimuli of a predetermined voltage is sent to actuator 140. More specifically, control circuit 208 initiates the process by directing signal generator 222 to send a signal (stimuli) to actuator 140. As this defined stimuli is predetermined, it has a known voltage and is applied to actuator 140.

As shown in step 304, the voltage across shunt resistor 205 is measured. As shown, for example, in FIG. 2A, shunt resistor 205 is connected on one side to actuator 140 and control circuit 208, and on the other side to ground. Therefore, control circuit 208 can measure the voltage across shunt resistor 205 since it is connected to shunt resistor 205 opposite to ground. As noted, control circuit 208 may include a digital signal processor (DSP). Therefore, shunt resistor 205 may be connected to, for example, a general purpose input output (GPIO) of control circuit/DSP 205, allowing the DSP to measure the voltage across shunt resistor 205. Alternatively, shunt resistor 205 may be connected to a microphone input on the DSP, which will also allow the DSP to measure the voltage across shunt resistor 205. For example, the DSP may include four or more microphone inputs, only one or two of which are connected to sound input device 126 for use to receive sound. Therefore, such a microphone input may be used to allow the DSP to measure the voltage across shunt resistor 205.

The use of control circuit 205 to measure the voltage across shunt resistor 205 is beneficial because the system does not further require a separate component or set of components to measure the voltage across shunt resistor 205. For example, it is not necessary for the system to include one or more voltage measurement circuits, voltmeters, potentiometers, oscilloscopes, or other devices to measure voltage. Since one side of actuator 140 is connected to ground, control circuit 208 may read the voltage across shunt resistor 205 while only being connected to one side of shunt resistor 205. Therefore, it is not necessary to provide, for example, a voltage measurement circuit to measure the voltage on both sides of shunt resistor 205. This device setup provides the benefit of requiring less components, which saves space and power consumption by the hearing prosthesis.

Referring back to FIG. 3A, after the voltage is measured across the shunt resistor, as shown in step 306, a second defined stimuli is sent to actuator 140. The second stimuli sent to actuator 140 in step 306 may be at a different frequency than the first stimuli sent to actuator 140 in step 302, or the second stimuli may be at the same frequency than the first stimuli, but may be sent at a different time than the first stimuli. These two possibilities are described further with respect to FIGS. 3B and 3C. Then, the voltage across shunt resistor 205 (i.e. the shunt component) is measured a second time in step 308.

Next, as shown in step 310 the voltage across shunt resistor 205 is calculated based on the measured voltage from step 304 and the measured voltage from step 308. The calculated voltage difference is then analyzed to determine a change in impedance across actuator 205, which can be analyzed to monitor problems or other characteristics/statuses of the actuator. For example, as noted, this impedance difference may be compared to the same calculated difference of a threshold, ideally stable actuator, or to the same calculated difference of the same actuator at a different point in time. If compared to a threshold, then the voltage difference would be compared to a value stored in memory, either in the control circuitry or elsewhere in system 200. If compared to the same calculated difference of the same actuator at a different point in time, the same process of steps 302-310 would be performed at that different point in time, and the voltage differences at those two different times would be compared.

Figure 3B:
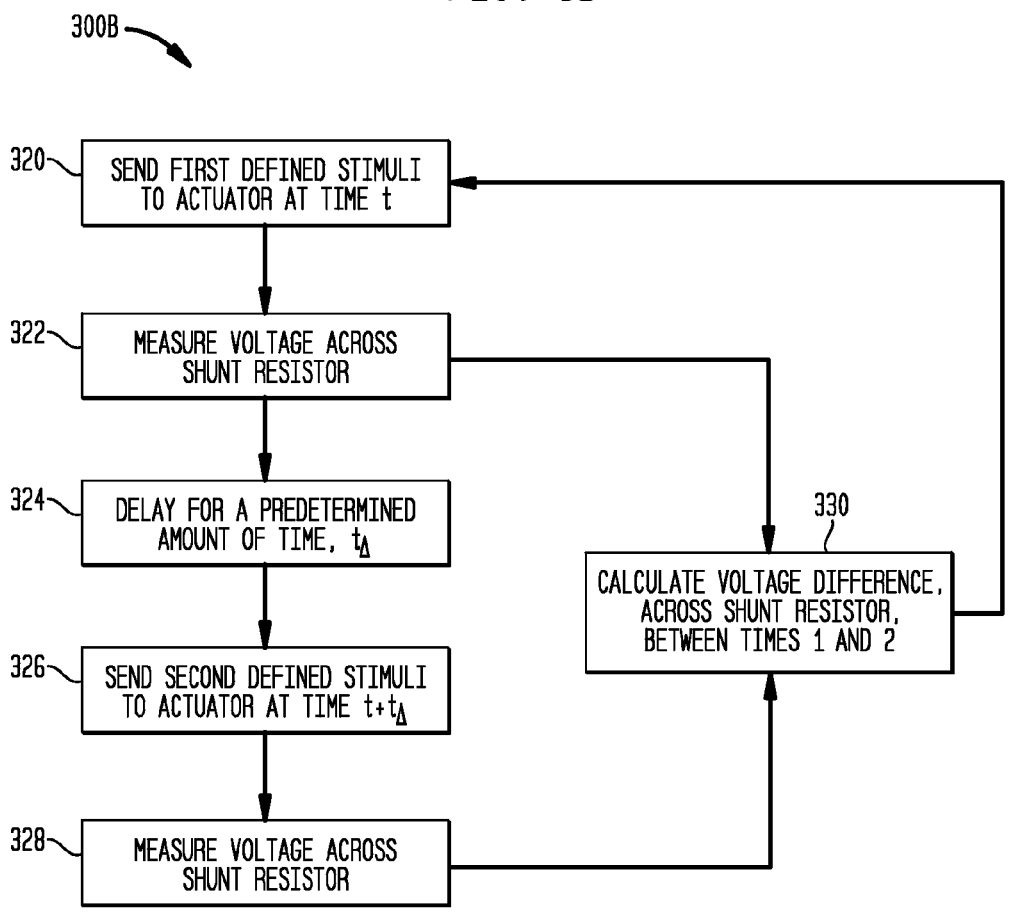
FIG. 3B is a flow chart of another exemplary method for determining a change in impedance across an actuator using a shunt component.

FIG. 3B is a flow chart 300B of another exemplary method for determining a change in impedance across actuator 140 using shunt resistor 205. As noted, observing the magnitude of the impedance of an actuator for changes over time may be used to make a determination of the state of the actuator. For example, an audiologist may observe magnitude impedance data from the recipient's actuator at a certain selected frequency, and then compare that data to similar data from the actuator at the same frequency at a later time. If a change in the magnitude of impedance across the actuator is different at the later time, then this change in impedance may indicate a change in state or characteristic of the actuator. FIG. 3B illustrates this exemplary method.

First, as shown in block 320, a first defined stimuli of a predetermined voltage is sent to actuator 140. More specifically, control circuit 208 initiates the process by directing signal generator 222 to send a signal (stimuli) to actuator 140. As this defined stimuli is predetermined, it has a known voltage and is applied to actuator 140.

As shown in step 322, the voltage across shunt resistor 205 is measured, similar to step 304 in FIG. 3A. Then, as shown in block 324, the system delays for a predetermined amount of time, labeled $t_A$. At block 326, a second defined stimuli of a predetermined voltage is sent to actuator 140 and, again, the voltage across shunt resistor 205 is measured at block 328. This process yields two measurements of voltage across the shunt resistor, each at a different point in time. As shown in block 310, the difference between these two measured voltages is then calculated. Such a voltage difference may be compared to a threshold voltage difference, or the measurement taken at the later time ($t+t_A$) may be compared to the earlier measured voltage. In either instance, as noted, any change in impedance may indicate a state or change in state of the actuator.

Figure 3C:
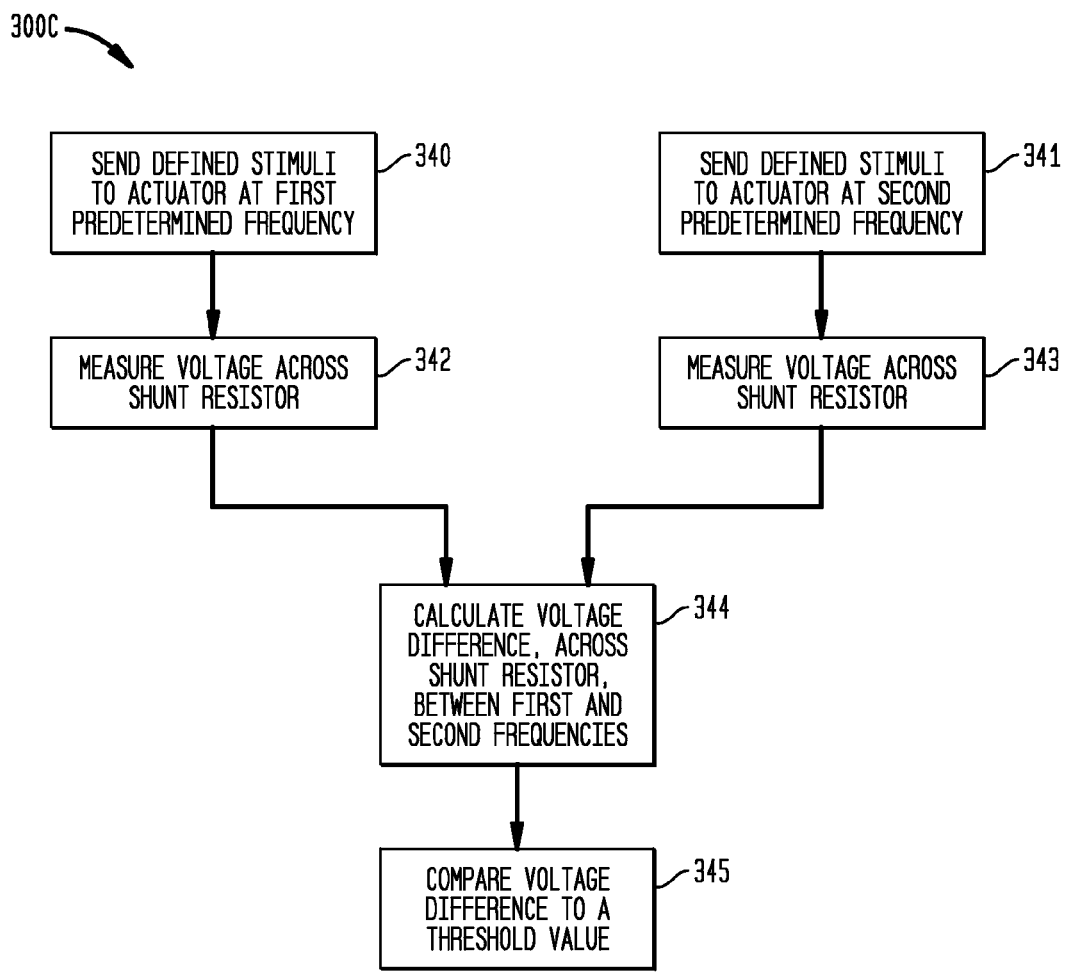
FIG. 3C is a flow chart of another exemplary method for determining a change in impedance across an actuator using a shunt component.

FIG. 3C is a flow chart 300C of another exemplary method for determining a change in impedance across actuator 140 using shunt resistor 205. As noted, observing the magnitude of the impedance of an actuator for changes between different frequencies may be used to make a determination of the state of the actuator. More specifically, the audiologist may read the magnitude of the impedance at two different frequencies, calculate the difference in magnitude between the two frequencies, and then, for example, compare that difference to a threshold. FIG. 3C illustrates this exemplary method.

First, as shown in block 340, a first defined stimuli of a predetermined voltage is sent to actuator 140. As shown in block 341, a second defined stimuli of a predetermined voltage is sent to actuator 140. The first and second stimuli sent to actuator 140 are sent at different, predetermined frequencies. After the first stimuli is sent to the actuator, as shown in block 342, the voltage across shunt resistor 205 is measured, similar to step 306 in FIG. 3A and step 322 in FIG. 2B. After the second stimuli is sent to the actuator, as shown in block 343, the voltage across shunt resistor 205 is measured.

Next, as shown in block 344, the difference between these two measured voltages is then calculated. Such a voltage difference may be compared to a threshold voltage difference, as shown in block 345, or may be compared to a similar difference previously taken between the same two frequencies. In either instance, as noted, any change in impedance may indicate a state or change in state of the actuator. In an exemplary embodiment, this threshold voltage can be stored in the device (e.g., can be part of an algorithm used to determine the change in the impedance).

Although FIGS. 3A-3C were not each described in the context of implementing each process of calculating a change in impedance across actuator 140 or of determining a state or characteristic of the actuator based on that change in impedance, it should be recognized that such methods should be considered as part of the scope of the present technology.

Figure 4:
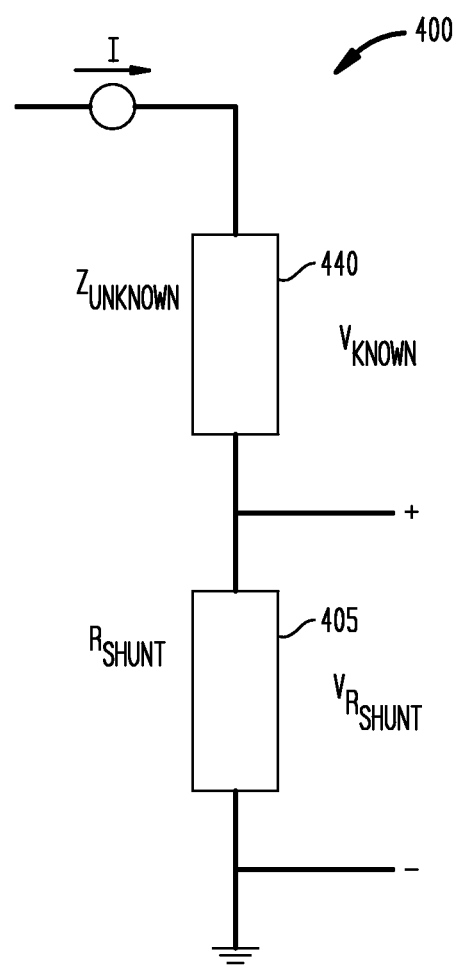
FIG. 4 illustrates a partial circuit diagram representative of the actuator and shunt resistor relationship in accordance with embodiments of the present technology.

Instead of measuring a change in voltage across shunt resistor 205 which, as described, is proportional to the current flowing through the system and is representative of a change in impedance across actuator 140, one may instead use the measured values of voltage across shunt resistor 205 to actually calculate that current and subsequently a change in electrical impedance of actuator 140. As noted, a change in electrical impedance presented by the actuator indicates a corresponding change in mechanical impedance of the actuator. FIG. 4 shows a partial circuit diagram, a voltage divider, representative of the actuator and shunt resistor relationship described above with respect to FIGS. 2A, 2B and 3. Circuit diagram 400 includes $Z_{unknown}$ 440, which represents the complex electrical impedance of actuator 140, and $R_{shunt}$ 405, which represents the resistance of shunt resistor 205. Furthermore, $V_{known}$, shown next to $Z_{unknown}$ 440 in FIG. 4, is the known voltage applied to actuator 140. $Z_{unknown}$ 440 is known because it is equal to the voltage stimulus applied to actuator 140 by signal generator 222, as described. $V_{Rshunt}$ represents a voltage, or a change in voltage, across $R_{shunt}$. Since the change in voltage across $R_{shunt}$ is proportional to the current through $R_{shunt}$, and therefore the current through actuator 140, the following equation may be used to determine $Z_{unknown}$:

$$Z_{unknown} = (R_{shunt} * V_{known}) / V_{Rshunt}$$

Since $R_{shunt} * V_{known}$ are known and $V_{Rshunt}$ is calculated, as described, $Z_{unknown}$ may be calculated.

As noted, the bone conduction device may also include a power source to give power to the different components of the external or implanted component, such as amplifier 217 shown in FIGS. 2A and 2B. When fully powered and in fully working condition, the power source applies a known voltage to the device components (at least partially resulting in a known $V_{known}$ as described above). However, if the power source has deteriorated over time, then the "known" voltage being applied may not accurately reflect the actual voltage being applied. Such deterioration may be detected using a built-in detector or a change in impedance in the system as described herein. This deterioration may be compensated for after detection in the calculation of the impedance across the actuator as described above.

As noted, once a change in impedance of an actuator in a vibrating hearing prosthesis has been detected and analyzed, that change in impedance may be used for various purposes. More specifically, data collected regarding the change in impedance of the actuator may be used to benefit the recipient and improve the performance of the hearing prosthesis. First, as noted, a change in impedance across actuator 140 may indicate a change in the stability of the implant. A change in stability of the implant may indicate one or more of several states or conditions of the implant, such as that the connection between the actuator and the skull of the recipient, has become looser than it was previously. An implant may become looser over time for various reasons. For example, an implant may become looser over time because the recipient fell or otherwise hit their skull and/or hearing prosthesis against a hard surface. This may especially be a problem for young children who tend to be more reckless than adults and do not protect themselves from damage and resultant trauma. If a child, or another recipient, were to experience trauma to the head, an audiologist or caretaker for the recipient (hereinafter, collectively, "the recipient") may initiate a test to measure the change impedance across the actuator. This data, including the change in impedance across the actuator, may be sent to the audiologist for analysis or may be viewed and analyzed on a computer by a caretaker for the recipient. If it is determined that the implant has become looser over time, then the recipient may choose to have the device re-attached to the skull or other remedies.

An implant may also become looser over time because the implanted site within the recipient has not healed correctly, causing osseointegration between the bone conduction device and the skull of the recipient to stall and even regress. The use of actuator impedance data to detect the status of osseointegration is discussed further below.

An implant may also become looser over time because the implant components may have corroded or otherwise become less structurally secure over time. For example, the coupling (such as coupling 161 in FIG. 1A), implanted anchor (such as implanted anchor 162 in FIG. 1A), or other abutment physically coupling the external portion of the bone conduction device to the recipient, or the actuator itself or other portions of the external component, may have worn over time and may need to be replaced. If it is determined that the implant has become looser over time, then the recipient may choose to have the whole device or parts of the device replaced.

An implant may also change stability by becoming more stable over time. For example, an implant may become more stable over time in the weeks and months after surgery, during which a surgeon implanted the bone conduction device into the recipient's skull. As such, a change in stability may indicate a change in the status of osseointegration between the implant and, in the case of a bone conduction device, the skull of the recipient. Osseointegration begins immediately after surgery and occurs over time until the implant is fully stable/implanted into the recipient. Therefore, if the surgery to implant the bone conduction device was successful, actuator 140 should be in its least stable state immediately after surgery and should become more stable over time. Therefore, a change in impedance across actuator 140 over time, such as a gradual and steady decrease in impedance, may indicate that the bone conduction device is successful osseointegrating with the skull of the recipient and the site of surgery is healing correctly. On the other hand, a constant or slowly decreasing impedance across actuator 140 over time may indicate that the bone conduction device is not osseointegrating with the skull of the recipient and/or the site of surgery is not healing correctly. If this state is determined, then the recipient may choose to adjust the implant or re-introduce the implant to the skull of the recipient in a different manner.

If the impedance across actuator 140 gradually and steadily decreases over time after implantation and is compared with a threshold, such as the predetermined impedance of an ideal device that has fully osseointegrated into the skull of the recipient, then this data may help a recipient or audiologist determine that the bone conduction device is ready to be operated for the first time. For example, the change in impedance across actuator 140 within a fully osseointegrated bone conduction device should be equal to or close to zero since the actuator in a fully osseointegrated device should be stable. On the other hand, if the impedance across the actuator in the bone conduction device is still changing over time, then use of the actuator, which would require vibration of the actuator, may cause the stability of the implant to decrease or prevent the implant from continuing to stabilize after surgery. Therefore, a recipient or audiologist may initiate a test to determine the impedance across the actuator in a recently implanted device to determine when the device is ready for use by the recipient.

Second, a change in impedance across actuator 140 may indicate what type of device the actuator is connected to. As noted, the actuator may be included in a bone conduction device that is coupled to the skull of a recipient using an abutment (including, for example, a coupling such as coupling 161 in FIG. 1A, an implanted anchor such as implanted anchor 162 in FIG. 1A, among others). When such an abutment is used, the bone conduction device, including the actuator, is rigidly coupled to the skull of the recipient. On the other hand, the actuator may be included in a softband bone conduction device that is configured to be worn around the recipient's head. When a softband is used, the actuator may be pushed against the recipient's skull to transmit vibrations to the skull, but is not rigidly connected to the skull. Since bone conduction devices using, for example, an abutment and a softband are coupled to the recipient's skull with different rigidities, the stability of the actuator in those devices will also be different. More specifically, an actuator in a softband bone conduction device will be generally be less stable than an actuator in a bone conduction device that couples the actuator to the skull of a recipient using an abutment. Therefore, an audiologist or recipient may initiate a test to determine the impedance across the actuator and compare that impedance to a threshold, such as the impedance across the actuator of a bone conduction device that has a known coupling mechanism.

Similarly, if the actuator is implemented into an external component that is indirectly connected to the recipient's skull by connecting the external component to the skin of the recipient adjacent to the skull using, for example, an adhesive, a change in impedance across the actuator may help detect if the adhesive is deteriorating over time. For example, an increase in mechanical impedance of the actuator over time may indicate an increase in instability, as noted, and the increase in stability may indicate that the adhesive is not securely holding the external component to the recipient's skin any longer. If the adhesive has become looser over time, the recipient may choose to replace the adhesive, or re-attach the external component to their skin using new adhesive.

Third, a change in impedance across actuator 140 may indicate whether the bone conduction device is being worn by the recipient or whether the bone conduction device has been disconnected from the recipient and is instead detached from the recipient (such as, for example, being held in the recipient's hand or lying on a table). Generally, bone conduction devices and other hearing prostheses include a user interface with user interface elements, such as buttons and switches, that allow the recipient and/or audiologist to control certain features of the bone conduction device. One example of a feature that the recipient and/or audiologist may control is whether the bone conduction device is turned "on" for when the recipient is wearing and using the hearing prosthesis, or "off" for when the bone conduction device is not being used. However, it is possible that the recipient may detach the bone conduction device, whether coupled to the recipient's head using an abutment or a softband, and forget to turn the device off. For example, a recipient may detach the bone conduction device before going to sleep at night and leave the device on a table. Forgetting to turn the device off when not being used for long periods of time will drain the battery within the bone conduction device and render the bone conduction device unusable the next time that the recipient chooses to use the device. An actuator within a bone conduction device vibrating freely without being connected to a recipient may also result in damage to the device.

Alternatively, after implementing embodiments of the present technology into the bone conduction device, the device may instead run periodic tests on the device, including collecting data on changes in impedance across actuator 140. For example, control circuit 208, which may include a DSP, may initiate a test of the bone conduction device by directing signal generator 222 to send a defined signal (stimuli) of a predetermined voltage to actuator 140, measuring the voltage across shunt resistor 205, and calculating changes in impedance across the shunt resistor and actuator over time, as described. These voltage measurements and changes in impedance may then be stored in memory within control circuit 208 or elsewhere within the bone conduction device. If a drastic change in impedance across actuator 140 is detected, as described with respect to FIG. 5A, then control circuit may conclude that the bone conduction device has been disconnected from the recipient and can opt to automatically turn off the bone conduction device. Such a conclusion can be drawn regarding a bone conduction device that is completely disconnected from the recipient because actuator 140 would vibrate free in air when vibrating, resulting in a high peak impedance, as described.

Similarly, if little or no impedance is detected across actuator 140, it may be determined that the actuator has temporarily failed or otherwise stopped working. Such a state of the actuator could be a serious problem for the recipient because the recipient may unexpectedly be unable to hear using the bone conduction device.

After a state of the bone conduction device has been detected, such as, for example, instability of the device, the device may notify the recipient that a problem exists in the bone conduction device. For example, the device may automatically send an alert to a remote device such as a smartphone. Such an alert would allow the recipient or audiologist to take action to fix any problem detected in the bone conduction device, or otherwise take action based on the state of the device. The device may also output an audible alert using a speaker or other transducer (not shown) to notify the recipient that a problem exists in the device.

Exemplary methods can be used with a bone conduction device such as that disclosed in U.S. patent application Ser. No. 13/723,802, filed on Dec. 21, 2012, naming Dr. Marcus Andersson as an inventor. With regard to that application, an exemplary bone conduction implant as detailed therein includes a bone fixture configured to screw into the skull bone, a skin-penetrating abutment and an abutment screw that is in the form of an elongate coupling shaft. The bone conduction device of that application is configured such that the operationally removable component is removably attached to the implant. This is accomplished via a coupler, a portion of which is included in the bone conduction implant, and a portion of which is included in the operationally removable component. In an exemplary embodiment, the operationally removable component snap-couples to the abutment. The abutment includes a recess formed by sidewalls thereof that has an overhang that interfaces with corresponding teeth of coupling apparatus. Teeth elastically deform inward upon the application of sufficient removal and/or installation force to the coupling apparatus. In the embodiment of the just-referenced application, the connection between the coupling apparatus and the abutment is such that vibrations generated by the operationally removable component (e.g., such as those generated by an electromagnetic actuator and/or a piezoelectric actuator, etc.) in response to a captured sound are effectively communicated to the abutment so as to effectively evoke a hearing percept, if not evoke a functionally utilitarian hearing percept. Such communication can be achieved via a coupling (sometimes referred to as a connection or coupler) that establishes at least a modicum of rigidity between the two components.

In this vein, the dimensions and/or geometries of the interfacing portions are, in at least some embodiments, are specific and highly tolerance to provide a utilitarian bone conduction hearing percept.

In an exemplary embodiment, there is a method that includes utilizing the techniques detailed herein to determine one or more characteristics of the coupling between the operationally removable component and the abutment. For example, determining that a change in the impedance of the actuator of the bone conduction device can be used to determine that the mechanical characteristics of the coupling have changed (e.g., in the case of a snap-coupling, the teeth of the coupling have worn down and/or the resiliency of the teeth has deleteriously changed and/or the abutment has worn down, etc.

Accordingly, there is a method, comprising determining a change in an actuator impedance based on a change in an electrical property of a system of which the actuator is apart, and determining one or more system characteristics based on the change in the actuator impedance, wherein the system characteristic(s) are attrition (e.g., wear, damage, fatigue) of the coupling between the implant and the operationally removable component (e.g., one or both of the components that form the coupling). In an exemplary embodiment, there is a method, comprising applying a first stimuli to an actuator that is part of a system, determining a change in voltage across a shunt component in series with the actuator, and determining one or more system characteristics based on the change in voltage, wherein the system characteristic(s) are attrition (e.g., wear, damage, fatigue) of the coupling between the implant and the operationally removable component (e.g., one or both of the components that form the coupling). In an exemplary embodiment, the system characteristic(s) are the dimensions and/or geometries and/or changes in the dimensions and/or changes in the geometries of the interfacing portions of the coupling. In an exemplary embodiment, the system characteristic(s) are a thickness and/or a change in the skin thickness of a passive transcutaneous system (i.e., the thickness of the skin between the external component and the internal component thereof). In an exemplary embodiment, the system characteristic(s) are a holding force and/or a change in the holding force between the external component and the internal component of a passive transcutaneous system. In an exemplary embodiment, there is a method corresponding to any of those detailed herein that further includes utilizing existing signals for start-up, program change or volume change of a given hearing prosthesis that provides known output signals. These signals are used to estimate the actuator impedance and compare the impedance with reference impedances (including prior measured impedances). In an exemplary embodiment, the signals are utilized such that the recipient is not exposed to additional signals beyond those that are currently present in hearing prostheses.

The technology described and claimed herein is not to be limited in scope by the specific preferred embodiments herein disclosed, since these embodiments are intended as illustrations, and not limitations, of several aspects of the technology. Any equivalent embodiments are intended to be within the scope of this technology. Indeed, various modifications of the technology in addition to those shown and described herein will become apparent to those skilled in the art from the foregoing description. Such modifications are also intended to fall within the scope of the appended claims.

What is claimed is:

1. A method, comprising:
   determining, using a shunt component, a change in an actuator impedance based on a change in an electrical property of a system of which the actuator is apart; and
   determining one or more system characteristics based on the change in the actuator impedance,
   wherein the shunt component is in series with the actuator and ground.

2. The method of claim 1, further comprising:
   generating a signal based on the determined change in the actuator impedance; and
   providing the generated signal to the actuator to cause actuation of the actuator to generate a hearing percept.

3. The method of claim 1, wherein determining the change in the actuator impedance comprises determining a difference in voltage between a first voltage and a second voltage.

4. The method of claim 1, further comprising comparing the determined change in impedance with a threshold.

5. The method of claim 1, further comprising comparing the determined change in impedance with a change in impedance of the actuator at a different point in time.

6. The method of claim 1, further comprising:
   determining that the actuator is a component in a percutaneous bone conduction device based on the determined one or more system characteristics.

7. The method of claim 1, method further comprising:
   determining that the actuator is unstable based on the change in impedance.

8. The method of claim 1, the method further comprising:
   determining that a hearing prosthesis has been physically disconnected from a recipient based on the change in impedance.

9. The method of claim 1, wherein the determined change in impedance corresponds to a decrease in impedance, the method further comprising:
   determining that the actuator is stable based on the determination that the change in impedance corresponds to an decrease in impedance.

10. The method of claim 1, the method further comprising:
    determining that a hearing prosthesis has substantially osseointegrated with a bone of a recipient based on the change in impedance.

11. The method of claim 10, further comprising determining that the recipient may use the actuator as a component of the hearing prosthesis without causing damage to the actuator or to the recipient based on the determination that the hearing prosthesis has substantially osseointegrated with a bone of the recipient.

12. The method of claim 1, further comprising:
    determining, based on the determined change in impedance, that the actuator is part of one of a softband bone conduction device, testband bone conduction device, test rod bone conduction device, an active transcutaneous bone conduction device or a passive transcutaneous bone conduction device.

13. The method of claim 1, further comprising:
    applying a first stimuli to the actuator at a first frequency; and
    detecting the change in the electrical property of the system, wherein
    the detected change in the electrical property of the system is based on the applied first stimuli to the actuator.

14. The method of claim 13, further comprising:
    applying a second stimuli to the actuator at a second frequency different from the first frequency, wherein the detected change in the electrical property of the system is based on the applied second stimuli to the actuator.

15. The method of claim 1, further comprising:
applying a first and second stimuli to the actuator at a plurality of frequencies over the operational frequency range of the actuator; and
detecting the change in the electrical property of the system, wherein
the detected change in the electrical property of the system is based on the first and second stimulus applied the actuator.

16. The method of claim 1, wherein the determined change in impedance is at least 10 ohms.

17. The method of claim 1, wherein the action of determining a change in the actuator impedance includes measuring an impedance across the actuator and comparing the measured impedance across the actuator to a previously measured impedance across the actuator.

18. A method, comprising:
applying a first stimuli to an actuator that is part of a system;
determining a change in voltage across a component in series with the actuator;
determining one or more system characteristics based on the change in voltage;
measuring a first voltage responsive to the first stimuli across the component;
applying a second stimuli to the actuator at a same frequency as that of the applied first stimuli but at a different temporal location than that of the first stimuli;
measuring a second voltage, responsive to the second stimuli, across the component; and
determining the change in voltage across the component based on the measured first and second voltage.

19. The method of claim 18, further comprising:
determining a change in impedance of an actuator based on the determined change in voltage.

20. The method of claim 19, wherein determining the change in impedance of the actuator comprises identifying a change in the phase of the impedance of the actuator.

21. The method of claim 18, further comprising utilizing the actuator to generate waves of fluid motion in a cochlea to activate hair cells of an organ of *corti* in a recipient to which the actuator is attached to evoke a hearing percept.

22. The method of claim 18, wherein:
the first stimuli is applied by a signal generator; and
the actuator is electrically located between the signal generator and the shut component.

23. The method of claim 18, further comprising:
determining an impedance across the actuator based on the determined change in voltage,
wherein the one or more system characteristics includes the impedance across the actuator.

24. The method of claim 18, wherein:
a control circuit is electrically connected to a location between the actuator and the shunt component; and
the action of applying the first stimuli to the actuator includes sending a signal from the control circuit to a signal generator to generate the first stimuli that is applied to the actuator.

25. A hearing prosthesis, the prosthesis comprising:
an actuator;
a signal generator configured to provide a signal to the actuator to cause actuation of the actuator; and
a control circuit configured to direct the signal generator to apply a first stimuli to the actuator;
wherein the control circuit is configured to:
determine a change in an electrical property of a system of which the actuator is apart; and
determine an impedance-related phenomenon of the actuator based on the determined change in the electrical property,
the system includes a shunt component, and
wherein at least one of:
the shunt component is connected with the actuator in series, and wherein the change in the electrical property is a change in voltage across the shunt related to the first stimuli; or
the change in the electrical property is a voltage difference across the shunt related to the first stimuli.

26. The auditory prosthesis of claim 25, wherein the system includes the shunt component connected with the actuator in series, and wherein the change in the electrical property is a change in voltage across the shunt related to the first stimuli.

27. The auditory prosthesis of claim 25, wherein the system includes the shunt component, and wherein the change in the electrical property is a voltage difference across the shunt related to the first stimuli.

28. The auditory prosthesis of claim 25, wherein the control circuit is configured to direct the signal generator to generate and provide a second stimulus, based on the determined impedance-related phenomenon, to the actuator.

29. The auditory prosthesis of claim 28, wherein the impedance-related phenomenon is at least one of a change in impedance or an impedance of the actuator.

30. The auditory prosthesis of claim 25, wherein the hearing prosthesis is a bone conduction device.

31. The auditory prosthesis of claim 25, wherein the actuator is configured to provide the mechanical stimulation to the recipient.

32. A method for determining a state of an actuator of a hearing prosthesis configured to deliver mechanical stimulation to a recipient, comprising:
measuring a first voltage across a shunt component in series with the actuator and ground;
comparing the first voltage with a second voltage; and
determining one or more characteristics of the hearing prosthesis.

33. The method of claim 32 further comprising identifying a change in impedance of the actuator based on the first voltage and the second voltage, wherein determining the one or more characteristics of the hearing prosthesis is based on the change in the impedance.

34. The method of claim 32, wherein the characteristic of the hearing prosthesis is that the actuator has decreased in stability with respect to a bone of the recipient.

35. The method of claim 32, wherein the characteristic of the hearing prosthesis is that the hearing prosthesis has been physically disconnected from the recipient.

36. The method of claim 32, wherein the characteristic of the hearing prosthesis is that the hearing prosthesis has fully osseointegrated with a bone of the recipient.

37. The method of claim 32, wherein the characteristic of the hearing prosthesis is that the hearing prosthesis is a bone conduction device wherein the actuator is connected to the side of the head of a recipient via a device as one of the group of: softband bone conduction device, testband bone conduction device, test rod bone conduction device, active transcutaneous bone conduction device and passive transcutaneous bone conduction device.

38. The method of claim 37, further comprising a resonance peak of a frequency response of the impedance of the actuator.

39. The method of claim 38, wherein determining one or more characteristics of the hearing prosthesis comprises comparing the resonance peak with a threshold resonance peak.

40. The method of claim 32 further comprising determining that the actuator of the hearing prosthesis is in a first state based on the determination of one or more characteristics of the hearing prosthesis.

41. The method of claim 32 further comprising actuating the actuator to provide the mechanical stimulation to the recipient.

42. The method of claim 32, wherein:
the shunt component is electrically located between the actuator and ground.

43. The method of claim 32, wherein:
the shunt component is an ammeter shunt.

* * * * *